United States Patent
Mito

(10) Patent No.: US 6,576,592 B1
(45) Date of Patent: Jun. 10, 2003

(54) HERBICIDE COMPOSITION

(75) Inventor: Nobuaki Mito, Kobe (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/980,861

(22) PCT Filed: May 29, 2000

(86) PCT No.: PCT/JP00/03460

§ 371 (c)(1),
(2), (4) Date: Dec. 7, 2001

(87) PCT Pub. No.: WO00/74487

PCT Pub. Date: Dec. 14, 2000

(30) Foreign Application Priority Data

Jun. 7, 1999 (JP) ............................................. 11-159560

(51) Int. Cl.[7] .......................... A01N 43/54; A01N 57/02
(52) U.S. Cl. ............................................................ 504/128
(58) Field of Search ................................. 504/128, 206, 504/278

(56) References Cited

U.S. PATENT DOCUMENTS

| 4,145,209 A | 3/1979 | Holm ............................. 71/92 |
| 4,772,608 A | 9/1988 | Sasse et al. ................. 514/275 |
| 4,859,229 A | 8/1989 | Wenger et al. ................. 71/92 |
| 5,502,070 A | 3/1996 | Fuchs et al. ................. 514/406 |
| 6,054,410 A | 4/2000 | Landes et al. .............. 504/134 |

FOREIGN PATENT DOCUMENTS

| CA | 2199846 | 3/1996 |
| JP | A 7-53313 | 2/1995 |
| JP | 07-053313 | 2/1995 |
| JP | 11-292717 | 10/1999 |
| JP | A 11-292717 | 10/1999 |
| WO | WO 93/04585 | 3/1993 |
| WO | WO 96/08151 | 3/1996 |
| WO | A1 97/31535 | 9/1997 |
| WO | A1 98/09525 | 3/1998 |
| WO | WO98/43480 | 10/1998 |
| WO | WO 01/39597 A2 | 6/2001 |
| WO | WO 01/85907 | 11/2001 |

*Primary Examiner*—S. Mark Clardy
(74) *Attorney, Agent, or Firm*—Birch, Stewart, Kolasch & Birch, LLP

(57) ABSTRACT

The present invention relates to a herbicidal composition containing as active ingredients 2-[2-chloro-4-fluoro-5-(3-methyl-2,6-dioxo-4-(trifluoromethyl)-1,2,3,6-tetrahydropyrimidin-1-yl)phenoxy]propionic acid ester, and glyphosate or its salt, and a method for controlling weeds comprising applying it to weeds. The herbicidal effect in the case where the present composition applied is synergistically increased compared with the cases where the each active ingredient is independently applied, therefore the present composition can control effectively a variety of weeds.

12 Claims, No Drawings

HERBICIDE COMPOSITION

This application is the national phase under 35 U.S.C. §371 of PCT International Application No. PCT/JP00/03460 which has an International filing date of May 29, 2000, which designated the United States of America.

TECHNICAL FIELD

The present invention relates to a herbicidal composition, especially, a herbicidal composition suitable for controlling weeds in fields of corn.

BACKGROUND ART

At the present time, numerous herbicides are commercially available and used. There are, however, many species of weeds to be controlled and their growth extends over a long time. For this reason, requested are herbicides with higher herbicidal activity, wider herbicidal spectrum, and no problems for phytotoxicity to crops.

DISCLOSURE OF INVENTION

The present inventor has intensively studied to find out excellent herbicides. As a result, he has found that various weeds growing in crop lands or non-crop lands can be effectively controlled by a herbicidal composition containing as active ingredients, 2-[2-chloro-4-fluoro-5-{3-methyl-2,6-dioxo-4-(trifluoromethyl)-1,2,3,6-tetrahydropyrimidin-1-yl}phenoxy]propionic acid ester (hereinafter, referred to as the present ester) and N-(phosphonomethyl)glycine (common name; glyphosate, hereinafter, referred to as glyphosate) or its salt. He has further found that the herbicidal activity is synergistically increased as compared with the cases where the active ingredient are independently used, and the herbicidal composition can, therefore, be applied at a lower amount; and that the herbicidal spectrum is expanded and especially, a wide variety of weeds in fields of corn can be controlled, thereby completing the present invention.

Thus, the present invention provides a herbicidal composition comprising as active ingredients, the present ester and glyphosate or its salt (hereinafter referred to as the present composition); and a method for controlling weeds which comprises applying them to weeds.

THE BEST MODE FOR CARRYING OUT THE INVENTION

The present ester which is one active ingredient of the present composition represents C1–C7 alkylester, C5–C6 cycloalkylester, C3–C6 alkenylester and the like. These compounds can be produced according to the method described in the following production example.

PRODUCTION EXAMPLE 1

In 70 ml of N,N-dimethylformamide, 6.7 g of 3-(4-chloro-2-fluoro-5-hydroxyphenyl)-1-methyl-6-trifluoromethyl-2,4(1H,3H)-pyrimidinedione was dissolved, and 4.2 g of potassium carbonate and 3.3 ml of methyl 2-chloropropionate were added to the solution, and then that was stirred for 1 hour at room temperature and for 45 minutes at 100° C. Thereafter, the reaction solution was poured into water, and that was extracted with ethyl acetate. The organic layer was washed with saturated sodium chloride solution, and after drying over anhydrous magnesium sulfate, was concentrated. The residue was subjected to silica gel column chromatography (eluent, hexane/ethyl acetate=3/1), and 5.82 g of methyl 2-[2-chloro-4-fluoro-5-{3-methyl-2,6-dioxo-4-(trifluoromethyl)-1,2,3,6-tetrahydropyrimidin-1-yl}phenoxy]propionate (hereinafter referred to as the compound A) was obtained.

The present ester except for the compound A can be obtained by conducting the similar operations as described in the above production example 1, with the exception of using the reaction reagent, examples described in the following table 1, in replace of methyl 2-chloropropionate.

Some of the present ester obtained by such methods are shown with that reaction reagent.

TABLE 1

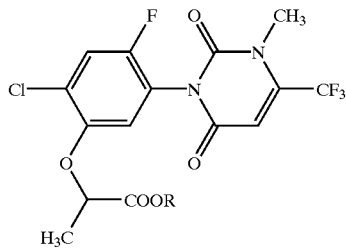

| Compound symbol | R | Reaction Reagent |
| --- | --- | --- |
| B | propyl | Propyl 2-bromopropionate |
| C | butyl | Butyl 2-bromopropionate |
| D | pentyl | Pentyl 2-bromopropionate |
| E | hexyl | Hexyl 2-bromopropionate |
| F | heptyl | Heptyl 2-bromopropionate |
| G | i-propyl | i-Propyl 2-bromopropionate |
| H | i-butyl | i-Butyl 2-bromopropionate |
| I | t-butyl | t-Butyl 2-bromopropionate |
| J | c-pentyl | c-Pentyl 2-bromopropionate |
| K | c-hexyl | c-Hexyl 2-bromopropionate |
| L | allyl | Allyl 2-bromopropionate |
| M | ethyl | Ethyl 2-bromopropionate |

(In this table, "i-" represents iso, "t-" represents tertiary, and "c-" represents cyclo.)

Compound A
$^1$H-NMR(CDCl$_3$,300 Mz): δ (ppm)7.31(1H,d,J=9.0 Hz), 6.82(1/2H, d,J=6.42 Hz),6.81(1/2H,d,J=6.45 Hz),6.35(1H, s),4.68(1H,q,J=6.9 Hz),3.74(3H,s),3.55(3H,s,br),1.66(3H,d, J=6.9 Hz)

Compound H
$^1$H-NMR(CDCl$_3$,250 Mz): δ (ppm)7.31(1H,d,J=8.9 Hz), 6.82(1/2H, d,J=6.5 Hz),6.81(1/2H,d,J=6.4 Hz),6.34(1H,s), 4.70(1H,brq,J=6.8Hz),3.98–3.85(2H,m),3.54(3H,q,J=1.2 Hz)1.90(1H,m),1.68(3H,d,J=6.8 Hz)0.862(3H,d,J=6.7 Hz), 0.858(3H,d,J=6.7 Hz)

Compound K
$^1$H-NMR(CDCl$_3$,300 Mz): 7.30(1H,d,J=8.9 Hz),6.82(1/2H,d,J=6.5 Hz),6.81(1/2H,d,J=6.4 Hz),6.33(1H,d,J=1.5 Hz),4.82(1H,m),4.66(1H,q,J=6.7 Hz),3.55–3.53(3H,m), 1.90–1.30(10H,m),1.66(3H,d,J=6.81 Hz)

Compound L
$^1$H-NMR(CDCl$_3$,300 Mz): δ (ppm)7.31(1H,d,J=8.9 Hz), 6.84(1/2H, d,J=6.50 Hz),6.82(1/2H,d,J=6.41 Hz),6.34(1H, s),5.91–5.80(1H,m), 5.29(1H,ddd,J=1.1 Hz,1.1 Hz,17.1 Hz),5.22(1H,dd,J=1.1 Hz,10.7 Hz), 4.71(1H,q,J=7.1 Hz), 4.64(2H,dd,J=1.1 Hz,5.6 Hz),3.55(3H,t,J=1.45 Hz),1.68 (3H,d,J=7.1 Hz)

Glyphosate and its salts are compounds described in Farm Chemicals Handbook, 1995 (Meister Publishing Co., 1995) page C188. The salts for the present invention mean all the agriculturally acceptable salts, and isopropylamine salt, trimesium salt, ammonium salt and the like can be exemplified.

The present composition has a herbicidal effect to a variety of weeds. Examples of the weeds are shown below.

Polygonaceous weeds:
wild buckwheat (*Polygonum convolvulus*), pale smartweed (*Polygonum lapathifolium*), pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)

Portulacaceous weeds:
common purslane (*Portulaca oleracea*)

Caryophyllaceous weeds:
common chickweed (*Stellaria media*)

Chenopodiaceous weeds:
common lambsquarters (*Chenopodium album*), kochia (*Kochia scoparia*)

Amaranthaceous weeds:
redroot pigweed (*Amaranthus retroflexus*), smooth pigweed (*Amaranthus hybridus*)

Cruciferous (brassicaceous) weeds:
wild radish (*Raphanus raphanistrum*), wild mustard (*Sinapis arvensis*), shepherdpurse (*Capsella bursa-pastoris*)

Leguminous (fabaceous) weeds:
hemp sesbania (*Sesbania exaltata*), sicklepod (*Cassia obtusifolia*), Florida beggarweed (*Desmodium tortuosum*), white clover (*Trifolium repens*)

Malvaceous weeds:
velvetleaf (*Abutilon theophrasti*), prickly sida (*Sida spinosa*)

Violaceous weeds:
field pansy (*Viola arvensis*), wild pansy (*Viola tricolor*)

Rubiaceous weeds: catchweed bedstraw (cleavers) (*Galium aparine*)

Convolvulaceous weeds:
ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)

Labiate weeds:
red deadnettle (*Lamium purpureum*), henbit (*Lamium amplexicaule*)

Solanaceous weeds:
jimsonweed (*Datura stramonium*), black nightshade (*Solanum nigrum*)

Scrophulariaceous weeds:
birdseye speedwell (*Veronica persica*), ivyleaf speedwell (*Veronica hederaefolia*)

Composite weeds:
common cocklebur (*Xanthium pensylvanicum*), common sunflower (*Helianthus annuus*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)

Boraginaceous weeds:
forget-me-not (*Myosotis arvensis*)

Asclepiadaceous weeds:
common milkweed (*Asclepias syriaca*)

Euphorbiaceous weeds:
sun spurge (*Euphorbia helioscopia*), spotted spurge (*Euphorbia maculata*)

Graminaceous weeds:
barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oat (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)

Commelinaceous weeds:
common dayflower (*Commelina communis*)

Equisetaceous weeds:
field horsetail (*Equisetum arvense*)

Cyperaceous weeds:
rice flatsedge (*Cyperus iria*), purple nutsedge (*Cyperus rotundus*), yellow nutsedge (*Cyperus esculentus*)

The present composition may be used as a herbicide, because of having herbicidal activities for a wide variety of weeds. The present composition gives excellent herbicidal effect, in which case the present composition are used in agricultural field, such as corn field, soybean field and the like, and non-agricultural field, such as orchard, horticultural field, play ground, vacant lot, wood, railroad side and the like.

The present composition can be used for till cultivation and no-till cultivation in the agricultural field. Especially the present composition can attain effective control of the wide variety of weeds growing between winter and spring and do not cause a problematic phytotoxicity against corn seeded after applying the present composition in which case the present composition was applied in the no-tillage cultivated corn field before seeding.

In the present composition, the mixing ratio of the present ester and glyphosate or its salt as active ingredients, although it may vary with the species of weeds to be controlled, situation and conditions of application and the like, is usually 1:1 to 500, preferably 1:2 to 100 by weight.

The present composition may be usually used in the form of formulations such as emulsifiable concentrates, wettable powders, flowables, granules and the like which can be prepared by mixing with solid carriers, liquid carriers, and the like, and if necessary, adding surfactants, other adjuvants and the like. In such a formulation, the present ester and glyphosate or its salt are usually contained at the total amount of 0.5 to 90% by weight, preferably 1 to 80% by weight.

The solid carrier to be used in the formulation may include, for example, the following materials in fine powder or granule form: clays (e.g., kaolinite, diatomaceous earth, synthetic hydrated silicon oxide, Fubasami clay, bentonite, acid clay); talc and other inorganic minerals (e.g., sericite, powdered quartz, powdered sulfur, activated carbon, calcium carbonate); and chemical fertilizers (e.g., ammonium sulfate, ammonium phosphate, ammonium nitrate, ammonium chloride, urea). The liquid carrier may include, for example, water; alcohols (e.g., methanol, ethanol); ketones (e.g., acetone, methyl ethyl ketone, cyclohexanone); aromatic hydrocarbons (e.g., toluene, xylene, ethylbenzene, methylnaphthalene); non-aromatic hydrocarbons (e.g., hexane, cyclohexane, kerosine); esters (e.g., ethyl acetate, butylacetate); nitriles (e.g., acetonitrile, isobutyronitrile); ethers (e.g., dioxane, diisopropyl ether); acid amides (e.g., dimethylformamide, dimethylacetamide); and halogenated hydrocarbons (e.g., dichloroethane, trichloroethylene).

The surfactant may include, for example, alkylsulfric acid esters; alkylsulfonic acid salts; alkylarylsulfonic acid salts; alkyl aryl ethers and their polyoxyethylene derivatives; polyethylene glycol ethers; polyhydric alcohol esters; and sugar alcohol derivatives.

The other adjuvants may include, for example, adhesive agents and dispersing agents, such as casein, gelatin, polysaccharides (e.g., starch, gum arabic, cellulose derivatives, alginic acid), lignin derivatives, bentonite, and synthetic water-soluble polymers (e.g., polyvinyl alcohol, polyvinyl pyrrolidone, polyacrylic acid); and stabilizers such as PAP (isopropyl acid phosphate), BHT (2,6-di-tert-butyl-4-methylphenol), BHA (2-/3-tert-butyl-4-methyoxyphenol), vegetable oils, mineral oils, fatty acids, and fatty acid esters.

The present composition can also be prepared by making each active ingredient into the above formulation and then mixing these formulations.

The present composition thus formulated may be applied to the plant as such, or after diluted with water or the like. Further, the present composition may also be used in admixture with other herbicides, in which case the herbicidal effect can be expected to be enhanced. Furthermore the present composition can also be used together with insecticides, fungicides, plant growth regulators, fertilizers or safener.

The application amount of the present composition, although it may vary with the mixing ratio of the present ester and glyphosate or its salt as the active ingredient compounds, weather conditions, formulation types, application times, application methods, application places, weeds to be controlled, and crops to be protected, is usually 10 to 8000 g, preferably 100 to 4000 g as the total amount of active ingredient compounds per hectare. In the case of emulsifiable concentrates, wettable powders, flowables, or the like, they are usually applied after diluted in their prescribed amounts with water at a ratio of 100 to 1000 liters per hectare. Also, in case of foliar treatment of the present composition to weeds, the dilution of the present composition with water in which the adjuvant is added may be expected to enhance the effect against weeds.

The following will describe formulation examples, in which parts are by weight.

Formulation Example 1

Four (4) parts of compound A, B, C, D, E, F, G, H, I, J, K, L or M, 80 parts of glyphosate or its salt, 3 parts of calcium lignin sulfonate, 2 parts of sodium laurylsulfate, and 11 parts of synthetic hydrated silicon oxide are well pulverized and mixed to give a wettable powder.

Formulation Example 2

Twenty (20) parts of compound A, B, C, D, E, F, G, H, I, J, K, L or M, 20 parts of glyphosate or its salt, 3 parts of calcium lignin sulfonate, 2 parts of sodium laurylsulfate, and 55 parts of synthetic hydrated silicon oxide are well pulverized and mixed to give a wettable powder.

Formulation Example 3

One-tenth (0.1) part of compound A, B, C, D, E, F, G, H, I, J, K, L or M, 50 parts of glyphosate or its salt, 3 parts of calcium lignin sulfonate, 2 parts of sodium laurylsulfate, and 44.9 parts of synthetic hydrated silicon oxide are well pulverized and mixed to give a wettable powder.

Formulation Example 4

Two (2) parts of compound A, B, C, D, E, F, G, H, I, J, K, L or M, 20 parts of glyphosate or its salt, 3 parts of calcium lignin sulfonate, 2 parts of sodium laurylsulfate, and 73 parts of synthetic hydrated silicon oxide are well pulverized and mixed to give a wettable powder.

Formulation Example 5

Two (2) parts of compound A, B, C, D, E, F, G, H, I, J, K, L or M, 40 parts of glyphosate or its salt, 3parts of polyoxyethylene sorbitan monooleate, 3 parts of CMC (carboxymethylcellulose), and 52 parts of water are mixed and wet pulverized until the particle size comes to 5 microns or smaller to give a flowable.

Formulation Example 6

Ten (10) parts of compound A, B, C, D, E, F, G, H, I, J, K, L or M, 10 parts of glyphosate or its salt, 3 parts of polyoxyethylene sorbitan monooleate, 3 parts of CMC (carboxymethylcellulose), and 74 parts of water are mixed and wet pulverized until the particle size comes to 5 microns or smaller to give a flowable.

Formulation Example 7

Zero point zero one (0.05) part of compound A, B, C, D, E, F, G, H, I, J, K, L or M, 25 parts of glyphosate or its salt, 3 parts of polyoxyethylene sorbitan monooleate, 3 parts of CMC (carboxymethylcellulose), and 68.95 parts of water are mixed and wet pulverized until the particle size comes to 5 microns or smaller to give a flowable.

Formulation Example 8

One (1) part of compound A, B, C, D, E, F, G, H, I, J, K, L or M, 10 parts of glyphosate or its salt, 3 parts of polyoxyethylene sorbitan monooleate, 3 parts of CMC (carboxymethylcellulose), and 83 parts of water are mixed and wet pulverized until the particle size comes to 5 microns or smaller to give a flowable.

The following will describe test examples.

Evaluation Criteria

The herbicidal effect is evaluated at 11 levels with indices of 0 to 10, i.e., shown by numeral "0", "1", "2", "3", "4", "5", "6", "7", "8", "9", or "10", wherein "0" means that there was no or little difference in the degree of germination or growth between the treated plants and the untreated plants at the time of examination, and "10" means that the test plants died completely or their germination or growth was completely inhibited. The values, "7", "8", "9", and "10" of the herbicidal effect mean a excellent herbicidal effect.

The phytotoxicity is evaluated like these, "no harm" means that the phytotoxicity was unrecognizable or almost unrecognized, "small" means that a slight degree of phytotoxicity was recognized, "medium" means that a medium degree of phytotoxicity was recognized, and "large" means that a large degree of phytotoxicity was recognized.

Test Example 1

Plastic pots each having a diameter of 11 cm and a depth of 8 cm were filled with upland soil, and then buried tubers of yellow nutsedge. And test plants were given 26 days to grow in greenhouse. An emulsifiable concentrate of compound A which had been obtained by well mixing 5 parts of compound A, 6 parts of Sorpol 3005X (produced by Toho Chemical Industry, Co., Ltd.) and 89 parts of xylene, a formulated glyphosate product (trade name: Roundup; seller, Monsanto Japan Limited), and a mixture of the emulsifiable concentrate of compound A and the formulated glyphosate product were independently diluted in their prescribed amounts with water. Each dilution was uniformly sprayed over the plants with a small sprayer, and then corn was further seeded. After the application the test plants were grown in the greenhouse for further 10 days and then, herbicidal activity and phytotoxicity to corn were examined. The results are shown in Table 2.

TABLE 2

| Test Compound | Dosage (g/ha) | Herbicidal activity Yellow nutsedge | Phytotoxicity Corn |
|---|---|---|---|
| Compound A | 120 | 4 | no harm |
| Glyphosate isopropylamine salt | 560 | 1 | no harm |
| Compound A + Glyphosate isopropylamine salt | 120 + 560 | 9 | no harm |

Industrial Applicability

The present composition have excellent herbicidal effect against a variety of weeds, especially it can control a wide variety of weeds in fields of corn selectively.

What is claimed is:

1. A herbicidal composition containing as active ingredients, 2-[2-chloro-4-fluoro-5-(3-methyl-2,6-dioxo-4-(trifluoromethyl)-1,2,3,6-tetrahydropyrimidin-1-yl)phenoxy]propionic acid ester, and N-(phosphonomethyl)glycine or its salt.

2. The herbicidal composition according to claim 1, wherein the ester is C1–C7 alkylester, C5–C6 cycloalkylester or C3–C6 alkenylester.

3. The herbicidal composition according to claim 1, wherein the ester is C1–C7 alkylester.

4. The herbicidal composition according to claim 1, wherein the ester is methyl ester.

5. The herbicidal composition according to any one of claims 1 to 4, wherein the weight ratio of the ester to N-(phosphonomethyl)glycine or its salt is from 1:1 to 1:500.

6. The composition of claim 1, further comprising at least one member from the group consisting of solid carriers, liquid carriers, surfactants and adjuvants.

7. A method for controlling weeds, which comprises applying the composition according to claim 1 to weeds.

8. The method for controlling weeds according to claim 7, wherein the weeds are those grown in fields of corn.

9. The method for controlling weeds according to claim 7, wherein the total amount of the active ingredient compounds per hectare is 10 to 8000 g.

10. The method according to claim 9, wherein the total amount of the active ingredient compounds per hectare is 100 to 4000 g.

11. The method according to claim 7, wherein said weeds are those grown in fields of soybean or corn.

12. The method according to claim 7, wherein said weeds are those grown in non-agricultural areas.

* * * * *